(12) United States Patent
Joshi

(10) Patent No.: US 7,930,036 B1
(45) Date of Patent: Apr. 19, 2011

(54) TACTILE APPLICATION OF HERBOELECTRICAL STIMULATION TO AUGMENT MAMMARY GLANDS

(76) Inventor: Pravin Joshi, Longwood, FL (US)

(*) Notice: Subject to any disclaimer, the term of this patent is extended or adjusted under 35 U.S.C. 154(b) by 471 days.

(21) Appl. No.: 12/034,792

(22) Filed: Feb. 21, 2008

Related U.S. Application Data (60) Provisional application No. 60/903,372, filed on Feb. 23, 2007.

(51) Int. Cl.
*A61N 1/20* (2006.01)
(52) U.S. Cl. .............................. 607/50; 607/64
(58) Field of Classification Search .................. 607/48, 607/50, 63–64
See application file for complete search history.

(56) References Cited

U.S. PATENT DOCUMENTS

| | | | |
|---|---|---|---|
| 3,500,832 A | | 3/1970 | Nunnery |
| 4,846,181 A | | 7/1989 | Miller |
| 4,895,154 A | | 1/1990 | Bartelt et al. |
| 5,324,317 A | * | 6/1994 | Reiss ............................... 607/67 |
| 5,458,625 A | * | 10/1995 | Kendall .......................... 607/46 |
| 5,484,387 A | | 1/1996 | Pitzen |
| 6,387,380 B1 | | 5/2002 | Knowlton |
| 6,947,791 B2 | | 9/2005 | Zhang et al. |
| 7,083,580 B2 | | 8/2006 | Bernabei |
| 7,162,297 B2 | | 1/2007 | Rossi |
| 2003/0177089 A1 | | 9/2003 | Giakoumakis |
| 2004/0059387 A1 | | 3/2004 | Yu |
| 2006/0224192 A1 | | 10/2006 | Dimmer et al. |
| 2006/0247559 A1 | | 11/2006 | Fei |
| 2007/0016277 A1 | | 1/2007 | Karat et al. |
| 2007/0020326 A1 | | 1/2007 | Walker et al. |
| 2008/0243060 A1 | * | 10/2008 | Hartmann et al. ............. 604/74 |

* cited by examiner

*Primary Examiner* — Niketa I Patel
*Assistant Examiner* — Rex Holmes
(74) *Attorney, Agent, or Firm* — Brian S. Steinberger; Law Offices of Brian S. Steinberger, P.A.

(57) ABSTRACT

Therapy and treatment devices, systems and methods for providing tactile and electrical stimulation to augment mammary glands and for making the tissues healthy and anti-carcinogenous. The devices, systems and methods combine both massage (tactile) stimulation with electrical current stimulation by electrodes to both augment mammary glands and for making the tissues healthy and anti-carcinogenous.

7 Claims, 11 Drawing Sheets

TACTILE APPLICATION OF HERBOELECTRICAL STIMULATION TO AUGMENT MAMMARY GLANDS

This invention claims the benefit of priority to U.S. Provisional Patent Application Ser. No. 60/903,372 filed. Feb. 23, 2007.

FIELD OF INVENTION

This invention relates to therapy, medical and healing treatments, in particular to devices, systems and methods for providing tactile and electrical stimulation to augment mammary glands making the tissues healthy and anti-carcinogenous.

BACKGROUND AND PRIOR ART

It has become increasingly popular over the years for woman to enlarge their breasts through surgical methods such as breast implantation surgeries. However, the cost of these medical treatments, the time it takes for recovery from the surgeries and the medical risks from damage caused by these surgeries makes these types of treatments undesirable to many women. Thus, there has been a growing need for non-surgical techniques to aid in breast augmentation.

In addition, women are often concerned with ailments such as breast cancer. Current medical procedures require the taking of a biopsy and often mastectomies as the recognized type of treatment. However, the cost of these medical treatments, the time it takes for recovery from the surgeries and the medical risks from damage caused by these surgeries makes these types of treatments undesirable to many women. Thus, there has been a growing need for non-surgical techniques to aid in cancer treatments and the need for preventative measures against breast cancer.

Various non-surgical stimulation techniques have been proposed over the years for that have included vibratory stimulation and direct electrical or thermal stimulation through electrodes.

In U.S. Publication 2007/0016277 to Karat; Carol et al., there is disclosed a lip augmentation device using an electric current and an iontophoretic delivery and composition.

In U.S. Publication 2007/0020326 to Walker; Jeffrey P. et al., there is disclosed a drug delivery system and method for the enhanced delivery of a therapeutic agent to which shows the placement of plurality of electrodes (desirable at least 7 and less than 15) within or surrounding predetermined three-dimensional region in body; region can be, tumor or other similarly diseased area; iontophoretic field.

In U.S. Publication 2006/0247559 to Fei; Daowei, there is disclosed a multifunctional mammary-gland-meridian frequency spectrometer which shows an electric device effective against mastitis, crater nipple and lobular hyperplasia.

In U.S. Publication 2006/0224192 to Dimmer; Steve et al., there is disclosed an electroporation device with two electrodes for delivery of an agent to a cell site.

In U.S. Publication 2004/0059387 to Vernon; Scott D. et al., there is disclosed an electro stimulation circuit for treating tissues.

U.S. Publication 2003/0177089 to Giakoumakis; Marianthi, shows breast augmentation with cocoa butter and Vitamin E.

U.S. Pat. No. 7,162,297 to Rossi describes an apparatus comprised of patches 4,4' with electrodes connected to wires 7a-7e; at other end of wires is electrical supply. The patches are placed on the part of the body to be treated over which the gel containing the substances to be delivered has been spread beforehand. Subject can carry out treatment. The treatment provides for effective passage of ionic substances through the skin.

In U.S. Pat. No. 7,083,580 to Bernabei; Gian Franco describes the application of electrical pulses and mechanical vibrations to the skin. To increase the absorption of substance that is applied at the same time to skin; ascorbic acid, collagen, skin treatment substances; ray of electrodes on vibratory plate, cancer; electrodes are applied to the skin. Device has on/off electrical pulses that reduce cellulite; piston of syringe subjects skin; liquid cream or drug is provided to subject's skin in a slow/controlled manner; allow substance absorbed within skin.

U.S. Pat. No. 6,947,791 to Zhang; Lei et al. describes cosmetic delivery of L-ascorbic acid-containing compositions to the layer of the skin wherein collagen formation takes place to enhance production of collagen and thereby combat some of the effects of aging, handheld electrical pulsar device with on/off button.

U.S. Pat. No. 6,387,380 to Knowton describes an ionic substance applied to skin; contact with thermal electrodes applied to skin; electrolytic solution transfer by RF energy from RF electrodes to underlying collagen tissues, skin tightening, and uses pours membrane for delivery of ionic solution; power source and controller with CPU.

U.S. Pat. No. 5,484,387 to Pitzen; Sylvester A. describes an electrical massage therapy hair growth; contemplates other uses where tissue loosening and improved blood circulation may improve a condition.

U.S. Pat. No. 4,895,154 to Bartelt; James T. et al. describes an electronic stimulation device for healing tissues includes two pairs of active electrodes and two pairs of electrodes for the return path.

U.S. Pat. No. 4,846,181 to Miller; Katherine H. describes an electro-stimulating device with electrodes placement on neck region and ankle and ionic solution.

U.S. Pat. No. 3,500,832 to Nunnery; Carroll J. describes a breast development jacket; warm weather circulates between two plies and enlarges the arteries and veins.

However, none of the above-cited references individually or in combination describe, teach or suggest effective non-surgical, outpatient treatments having little to no recovery times, that provide both breast augmentation and make the mammary tissues healthy and anti-carcinogenous.

Thus, the need exists for solutions to the above problems with the prior art.

SUMMARY OF THE INVENTION

A primary objective of the present invention is to provide non-surgical devices, systems and methods to augment mammary glands and make the tissues healthy and anti-carcinogenous.

A secondary objective of the present invention is to provide devices, systems and methods of tactile and electrical stimulation to augment mammary glands and make the tissues healthy and anti-carcinogenous.

A third objective of the present invention is to provide devices, systems and methods that combine massage techniques with electrical stimulation to both augment mammary glands and make the tissues healthy and anti-carcinogenous.

A fourth objective of the present invention is to provide inexpensive non-surgical devices, systems and methods to augment mammary glands and make the tissues healthy and anti-carcinogenous.

A fifth objective of the present invention is to provide outpatient treatments having almost no recovery time, non-surgical devices, systems and methods to augment mammary glands and make the tissues healthy and anti-carcinogenous.

A treatment system for breast tissue, can include a tactile stimulator for tactile stimulating the breast tissue of a subject, and an electrical generator for generating electrical current to the subject, wherein the tactile stimulator and the electrical generator provides breast augmentation to the breast tissue and to make the breast tissue anti-carcinogenous.

Tactile stimulation can occur by an herbal based solution and/or oil formulated for the breast tissue being rubbed into the breast tissue by the subject.

Electrodes can be attached to the subject to receive an electrical current from the electrical generator. Clips or clamps can be used for attaching the electrodes to ears and hands of the subject. The hands and ears are thought to facilitate breast augmentation and act as on and off switches and electrical conduits in the body.

A novel method of combining both tactile stimulation and electrical generation through the electrodes is also disclosed.

Further objects and advantages of this invention will be apparent from the following detailed description of the embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Figure 1:
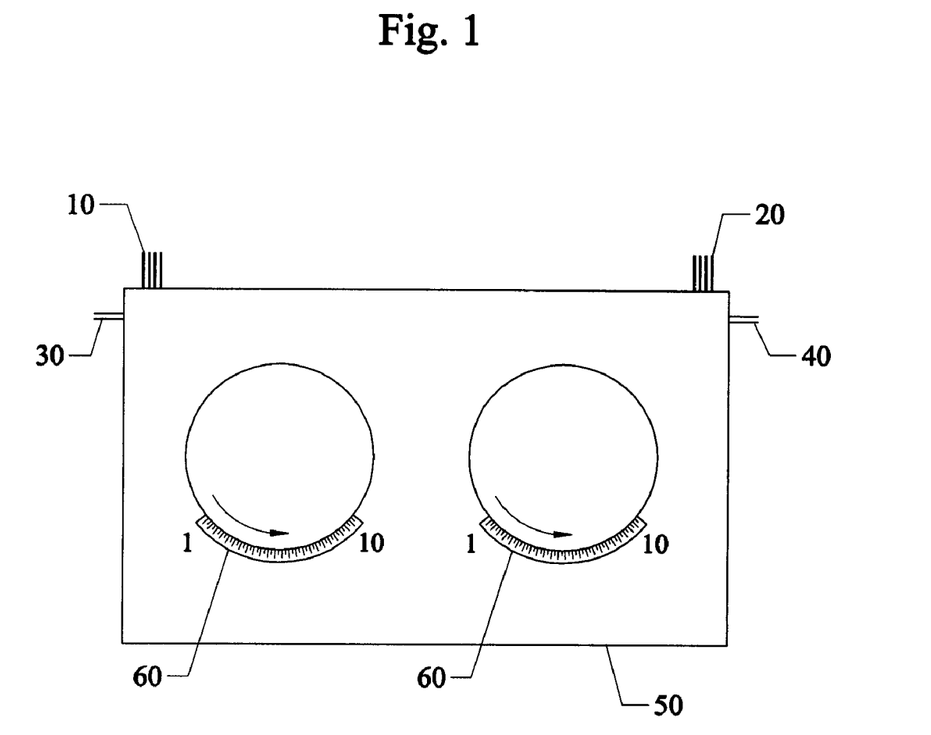
FIG. 1 shows a front outside view of the electrical generator.

FIG. 1 shows a front outside view of the electrical generator device 50. The electrical generator device 50 can, for example, be made of a rectangular plastic casing with dual isolated channels 60 for controlling the current of the positive and negative electrodes. For example, the generator may use a 9 volt alkaline battery with dual isolated channels 60, and can generate, for example, from about 10 to about 1000 microamperes, that are continuously adjustable. One pair of negative electrodes 10 are placed on the right and left ear of the subject. One pair of negative electrodes 20 are placed on the backs of the left and right hands of the subject. Additionally, two positive electrodes 30 and 40 are placed on the subject's thoracic spine between the $4^{th}$ and $7^{th}$ vertebrate.

Figure 2:
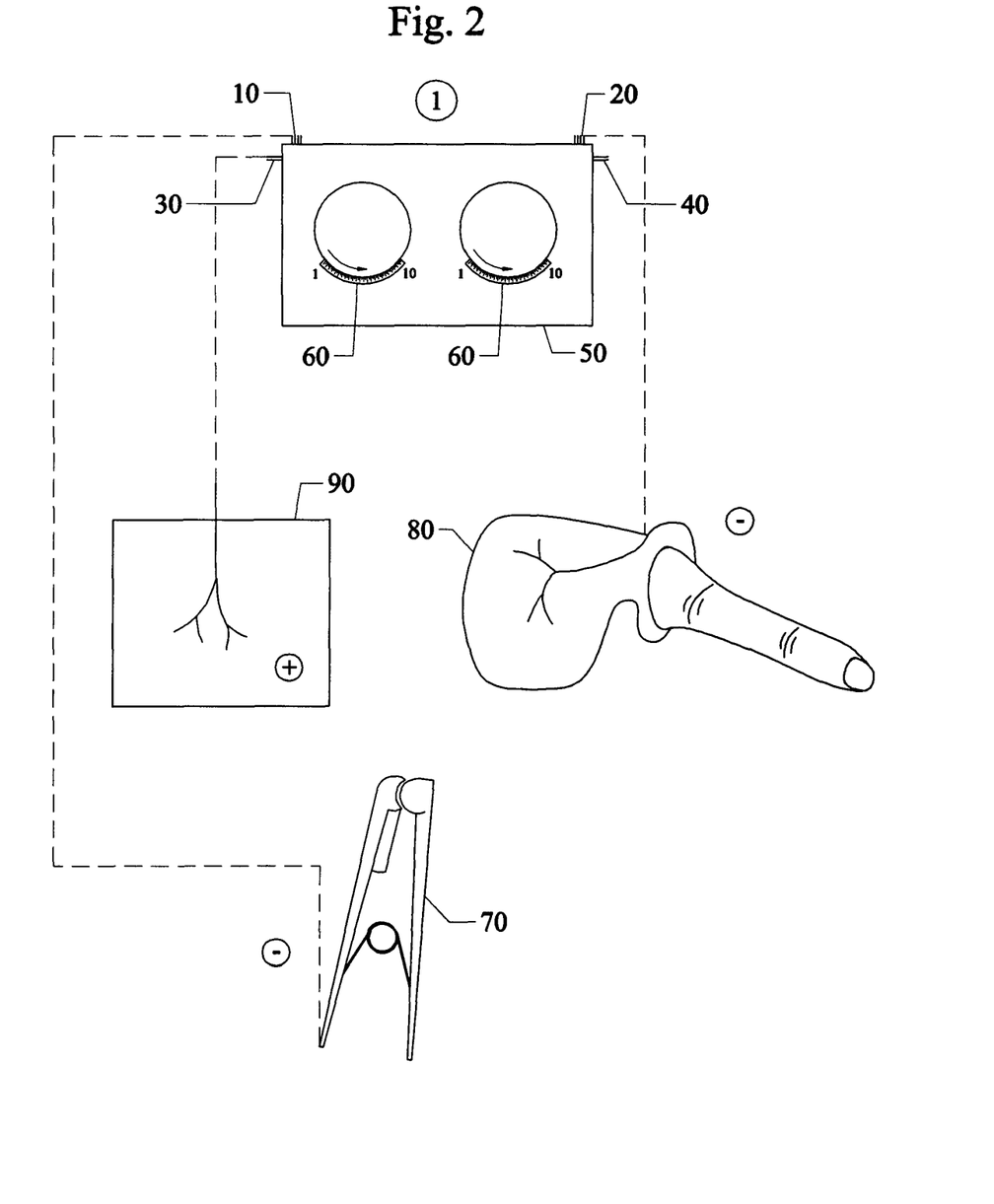
FIG. 2 shows front view of the electrical generator.

FIG. 2 shows a front view of the electrical generator device 50 with on pair of negatively charged electrodes 10 going to auricular electrode lead 70 and the other negatively charged pair of electrodes passing to the ring finger lead 80 on the dorsum of the left and right hands. As also illustrated in FIG. 2, the positively charged electrodes 30 and 40 pass to rectangularly shaped electrodes 90 attached to the thoracic spine between the 4th and $7^{th}$ vertebrate and directly behind each of the subject's breasts. In embodiments, the electric generator 50 with dual isolated channels 60 controls the electricity that can be applied to the different pairs of electrodes. One dial can supply power to an electrode pair each attached to one ear and one hand of the subject, and the second dial can supply power to another electrode pair, where each is attached to another ear and to another hand of the subject.

Figure 3:
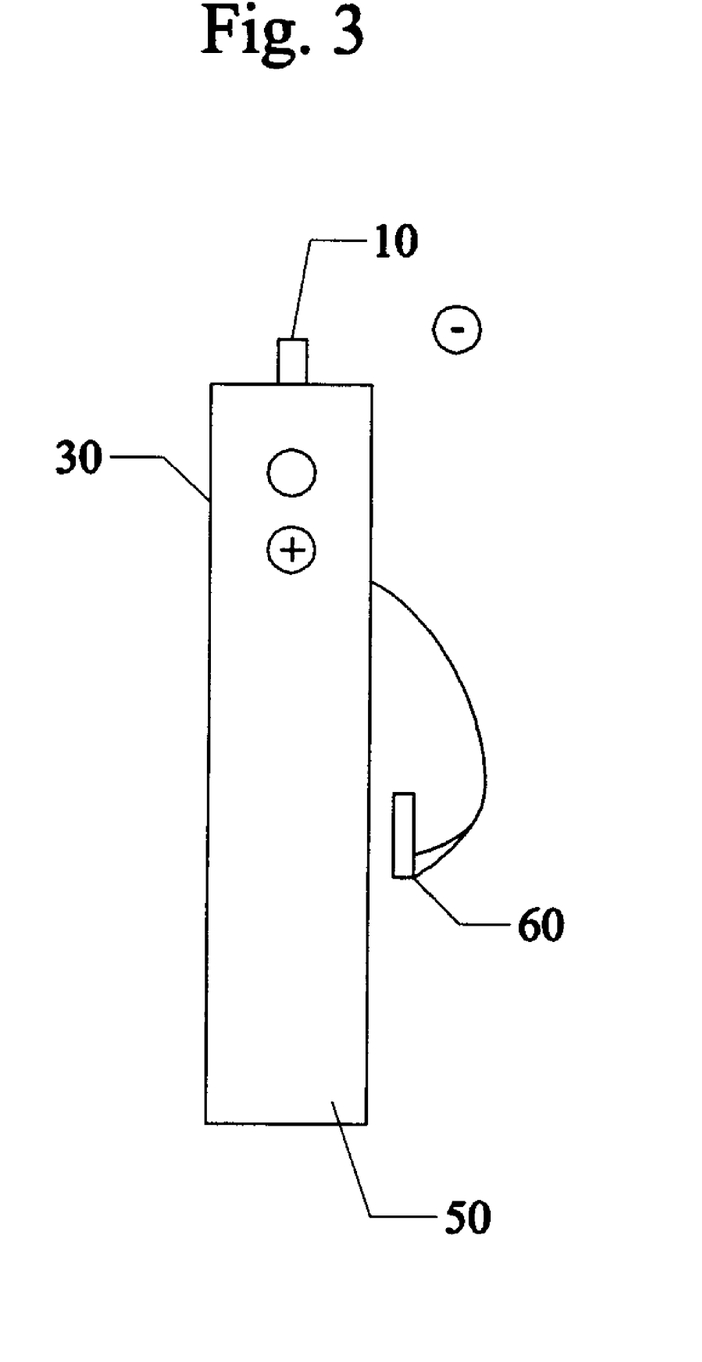
FIG. 3 shows a side view of the electrical generator.

FIG. 3 shows a side view of the electric generator device 50 with dials 60, negative electrodes 10, and positive electrodes 30.

Figure 4:
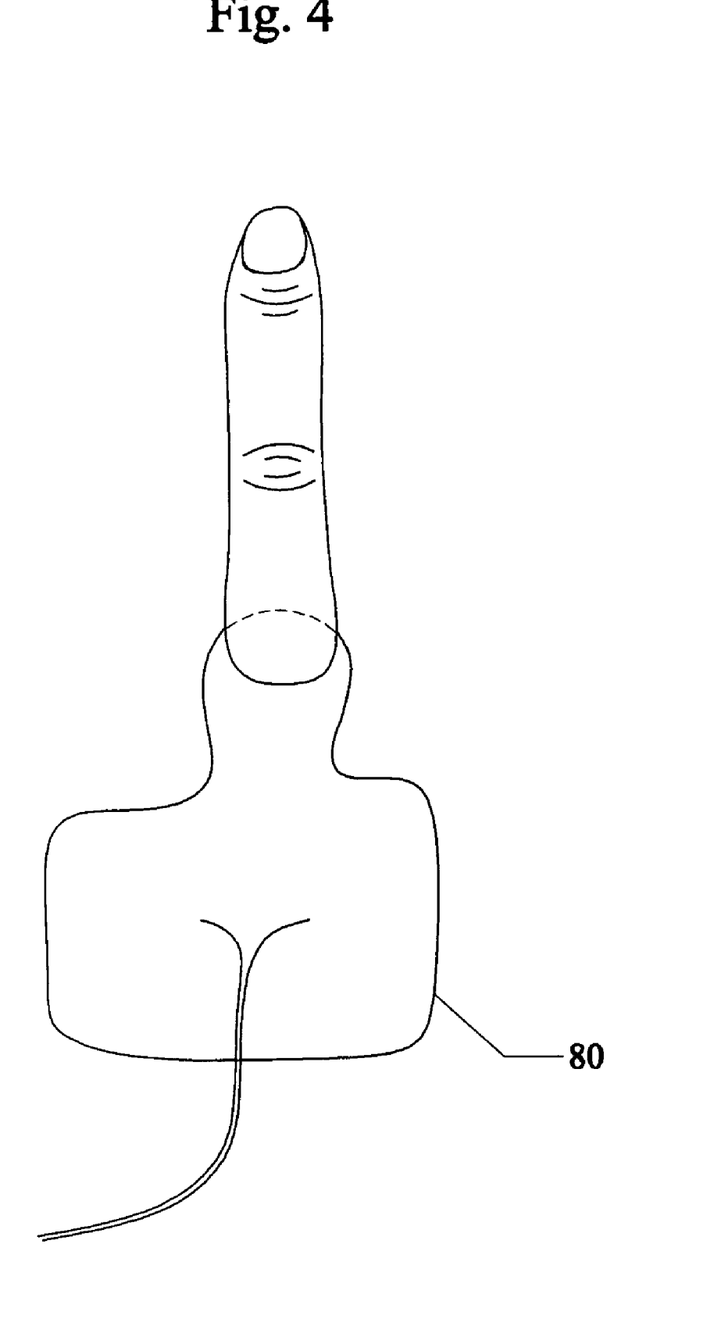
FIG. 4 shows a negative ring finger electrode, one electrode for each finger.

FIG. 4 illustrates the negatively charged ring finger electrode lead 80 placed on the dorsum of both of the subjects hands.

Figure 5:
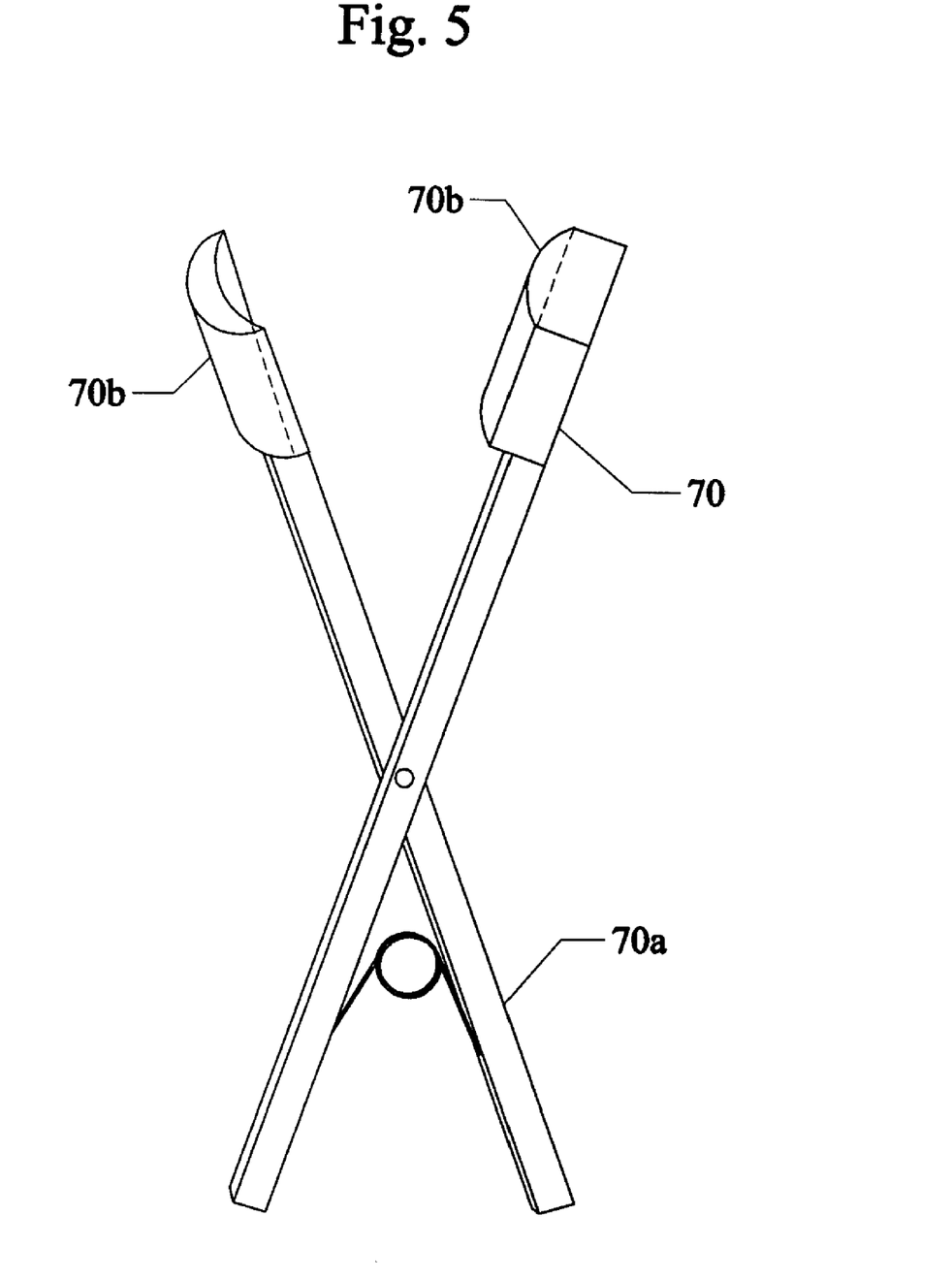
FIG. 5 shows the negative charged auricular electrode, one for each ear.

FIG. 5 shows a negatively charged auricular electrode leads 70 for attachment to both the left and right ears of the subject. The auricular electrode leads 70 comprise a concave surface that is placed on the anterior aspect of the auricular region. The convex surface is place on the posterior aspect of the auricular surface. The stem of the electrode lead 70a is insulated with a rubber sleeve up to the surface of the concave and convex contacts 70b.

Figure 6:
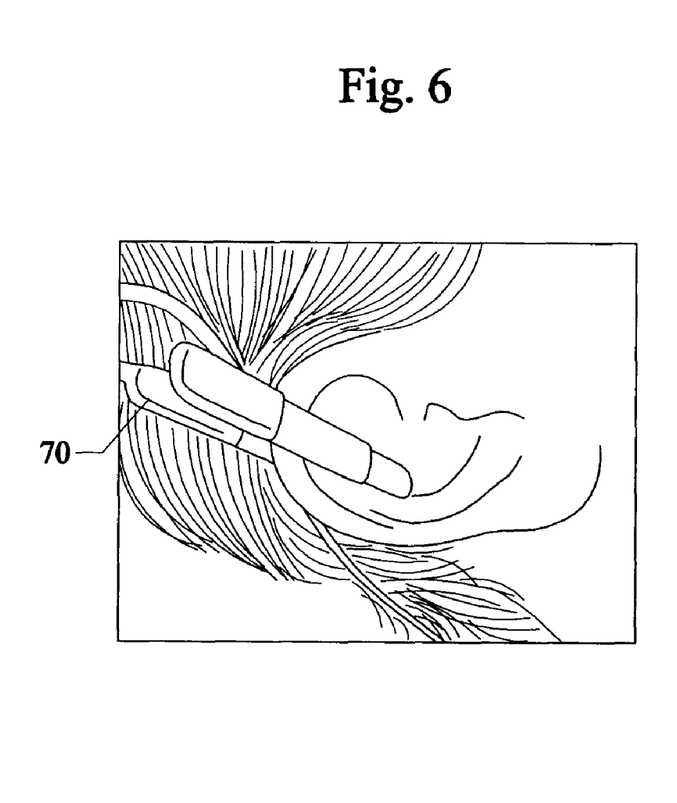
FIG. 6 shows the placement of an electrode on a subject's ear.

FIG. 6 shows the negatively charged auricular electrode lead 70 attached to a subjects auricular region.

Figure 7:
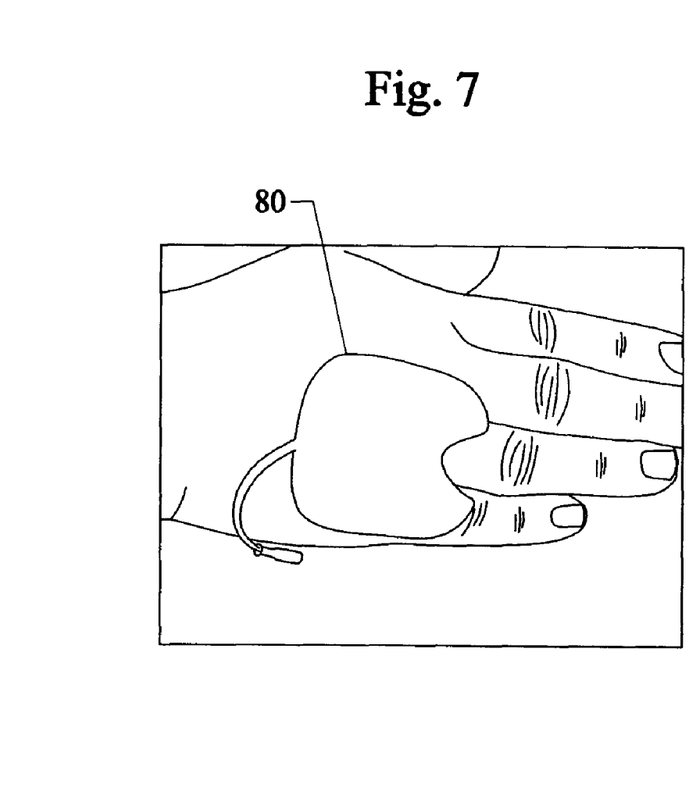
FIG. 7 shows placement of an electrode slipped over a fourth (ring) finger.

FIG. 7 illustrates the negatively charged ring finger electrode 80 placed on the dorsum of a subjects hand.

In embodiments, a first pair of electrodes may be attached to one ear and one hand of the subject, and the second pair of electrodes can be attached to another ear and another hand.

Figure 8:
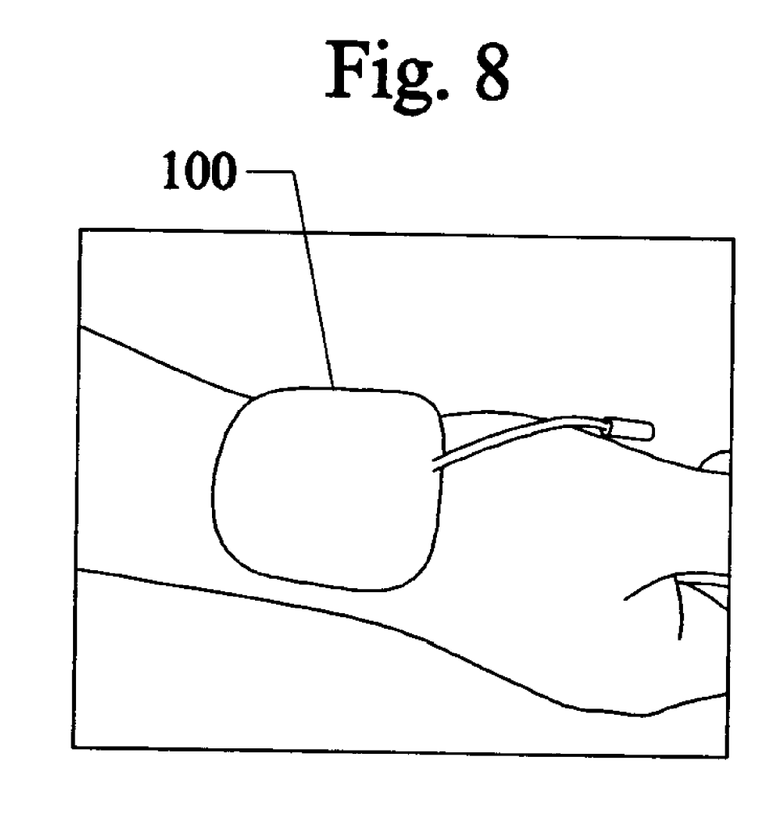
FIG. 8 shows the placement of an electrode on a subject's wrist.

FIG. 8 illustrates an alternative embodiment of the present invention. In this embodiment, a third party massages the soft tissue of the breasts of the subject. The third party is fitted with a negatively charged electrode 100 that is placed on the radial aspect of each wrist. Referring to FIGS. 1-3 and 8, the negatively charged electrode lead 100 connects to the electric generator 50 with dual isolated channels 60 at 20. The negatively charged ring finger electrode 80 is also in use in this embodiment.

Figure 9:
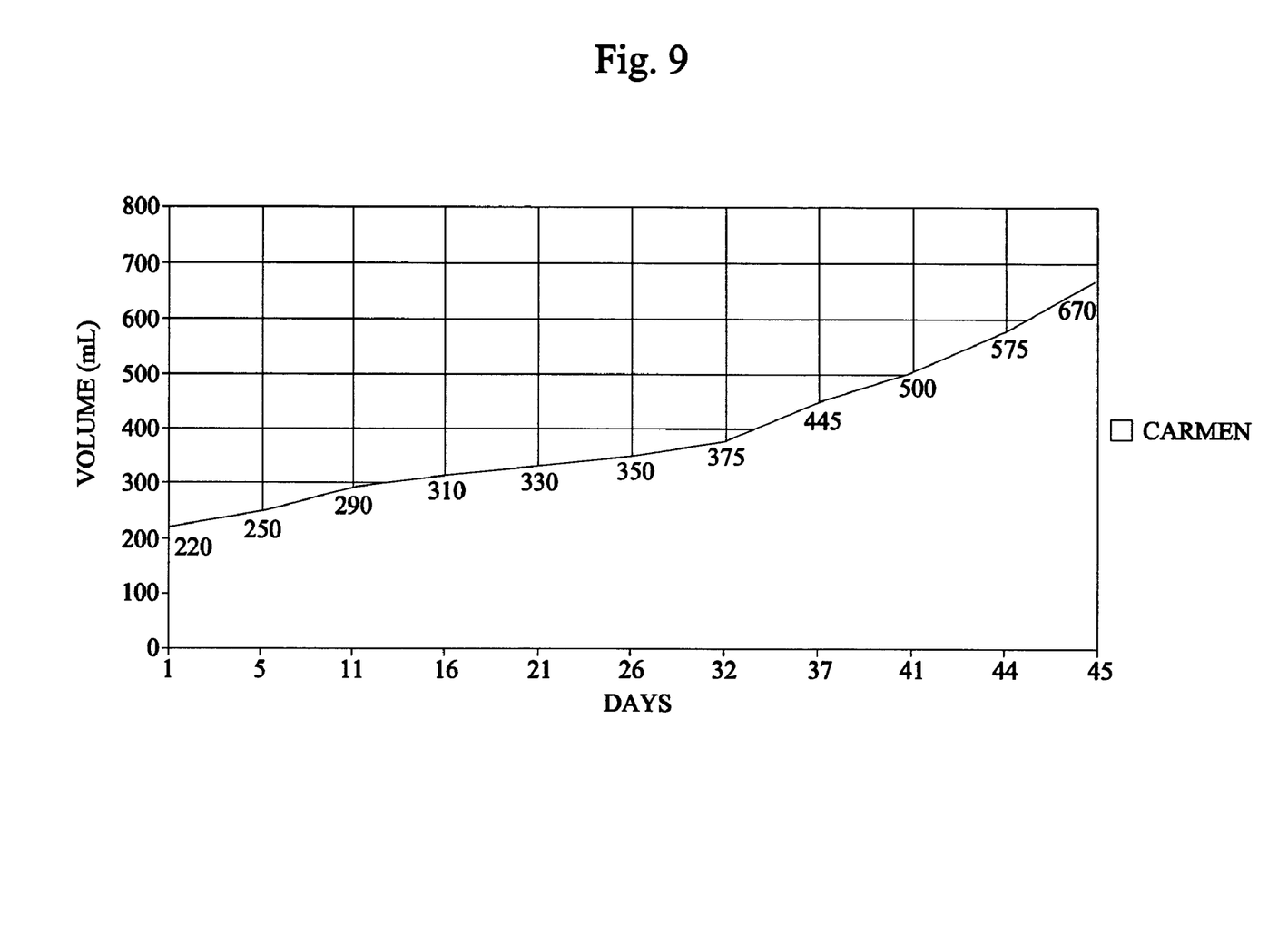
FIG. 9 shows a forty-five day growth chart of a female subject Carmen.

Referring to FIG. 9, there is illustrated a growth chart which indicates breast volume increase of the subject Carmen over a forty-live day span.

Figure 10:
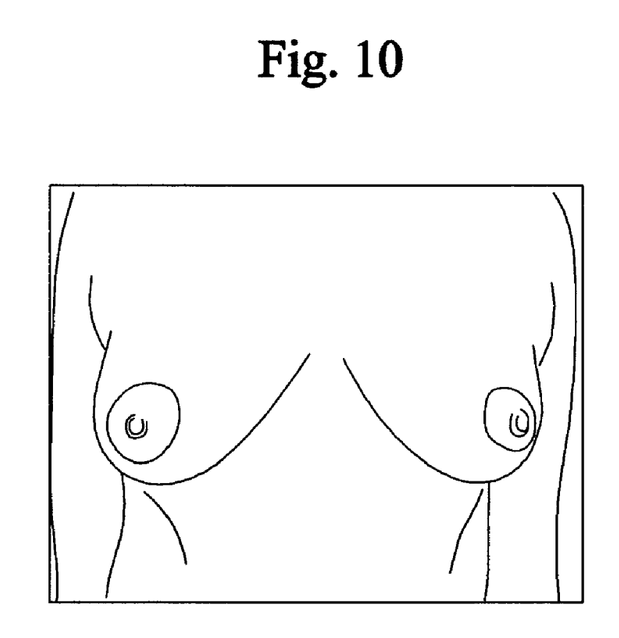
FIG. 10 shows subject Carmen on "day one" before application of herboelectric stimulation.

FIG. 10 shows black and white photographs of subject Carmen on "day one".

Figure 11:
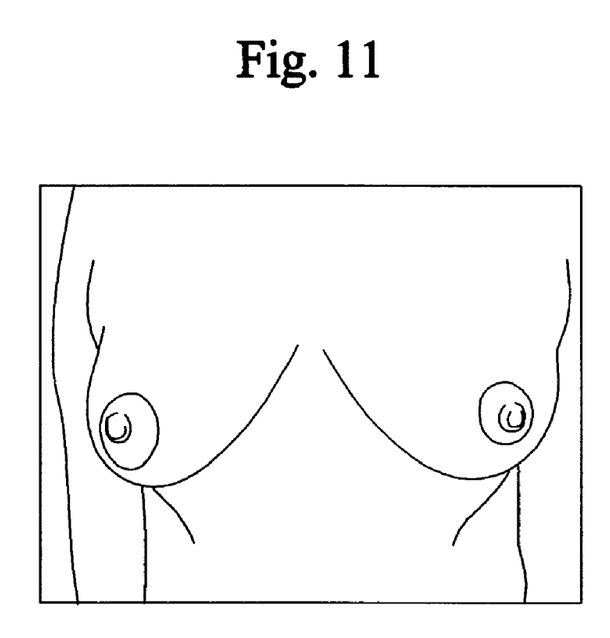
FIG. 11 shows subject Carmen on "day forty-five" after application of herboelectric stimulation.

FIG. 11 shows black and white photographs on "day forty-five" after application of the herboelectric stimulation. Photographs indicate an increase in breast volume as a result of the stimulation.

Figure 12:
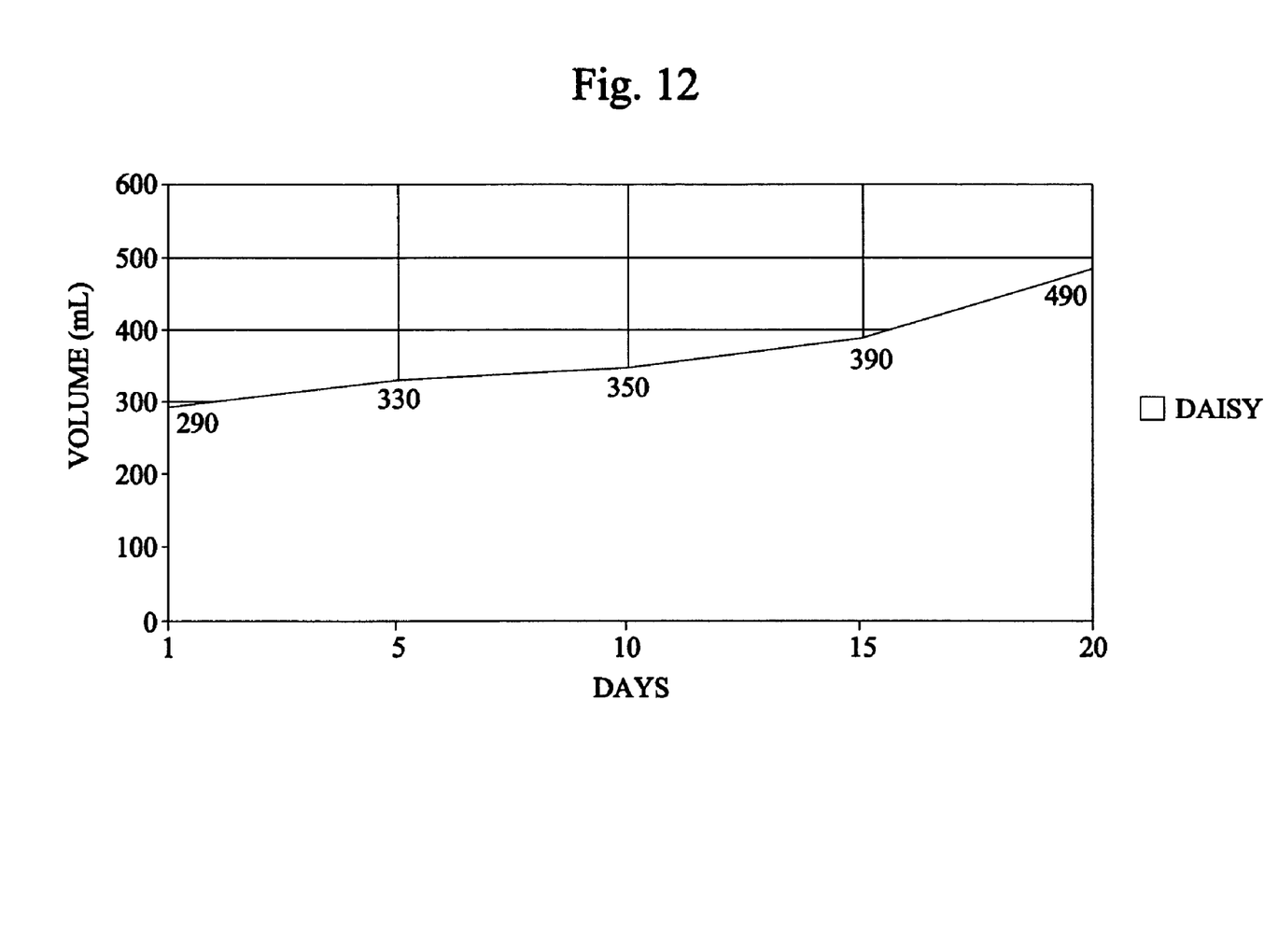
FIG. 12 shows a forty-five day growth chart of a female subject Daisy.

FIG. 12 shows a forty-five day growth chart of a female subject Daisy. The graph indicates the progressive breast volume increase over time.

Figure 13:
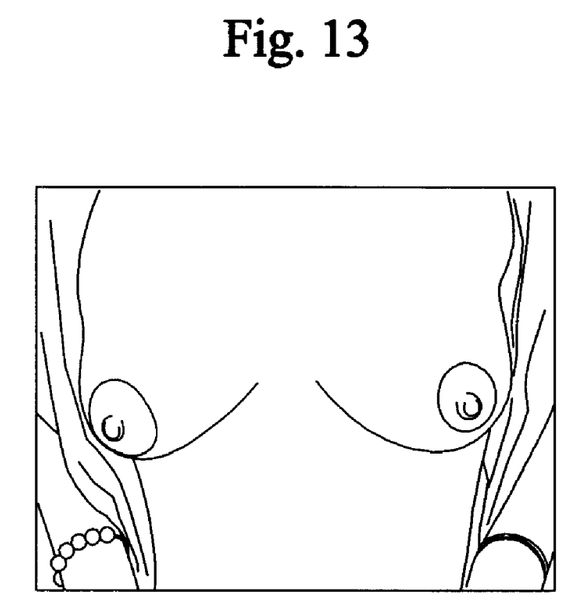
FIG. 13 shows subject Daisy on "day one" before application of herboelectric stimulation.

FIG. 13 shows black and white photographs of subject. Daisy on "day one".

Figure 14:
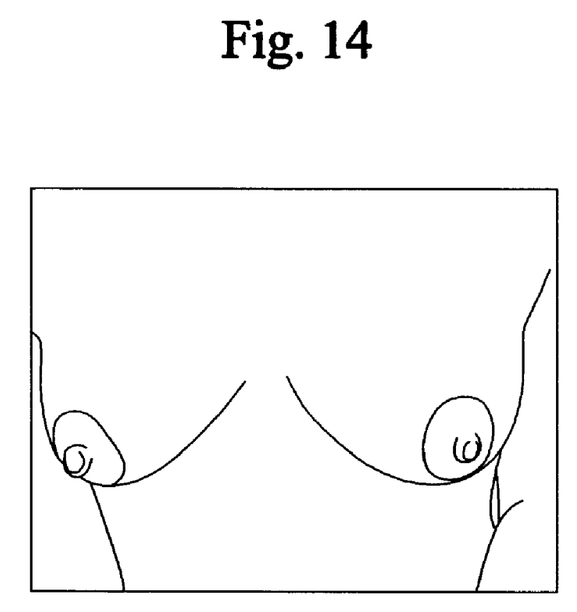
FIG. 14 shows subject Daisy on "day twenty" after application of herboelectric stimulation.

FIG. 14 shows subject Daisy after twenty days of herboelectric stimulation. Photographs show the increase in breast volume over the course of treatment.

Mammary glands augmentation occurs through tactile stimulation, together with herbo-electrical stimulation, which develops anticarcinogenous tissue.

In embodiments, the breast is defined as the organ which covers the entire chest wall or an upper rib cage and spherical in shape.

The breasts may be augmented non-surgically using three stimulants, for example, chemical electrical and mechanical by using these stimulants on the surface of the mammary glands facilitating the growth of the glands from about 0.5 milliliters to about 3 milliliters per day.

In embodiments, one pair of electrodes may be attached, for example, to one hand left and one hand right, and a second electrode pair may be attached, for example, to the other left and right ear. The ear electrode may be placed, for example, from about 2 to about 5 millimeters above the helix notch on the auricular region of the ear. The system, device and method, in embodiments allows for placing another electrode at the dorsum of the subject's spine between the $4^{th}$ through the $7^{th}$ thoracic vertebrate. In other embodiments, when a third party provides the soft tissue manipulation and massage, a pair of electrodes may, for example, be placed on the dorsum of hand at the base of lateral border of the 4th metacarpophalangeal joint and the distal aspect of the $4^{th}$ metacarpal joint or region. The electric current is applied according to the parameters set forth in TABLE II.

Micro current is supplied by the electric generator 50 with dual isolated channels 60. The micro current is turned on by rotating the dual isolated channels 60 in a counter-clockwise direction. The current is increased to point that the subject can tolerate comfortably. Comfort levels will vary with subjects. Some subjects will find the current well-tolerated while other will go through an adjustment period, for example, of from about a few minutes to a few days. Micro current from the electrical generator can range, for example, from about 0.8 to about 300 microamps, at a frequency of from about 0.5 to about 550 hertz. This current was applied to the subject via the dorsum of the hand and ear. Application of the current was applied from the superior (closest to the head) to inferior (closest to the feet) direction.

Embodiments of the present invention use a natural coupling mixture that is specially formulated for breast tissue. The mixture may include for example, a mixture comprised of the exocarp or pericarp of punica granatum (pomegranate). The mixture further comprises one part pulp of punica granatum and one part brassica juncee (mustard plant) extract and four part water, which aids in the mixing process. In embodiments, the external rind of the pomegranate is mixed with the oil of the mustard plant and water until well mixed. The mixture is then heated to boiling until it is dark brown or black in color. The mixture is then cooled to room temperature and liberally applied to the breast surface, After the coupling mixture is liberally applied to the breast tissue, the massage technique can include the subject moving their hands in a massage of the breast. The subject may, for example, massage the breast in opposite direction from the base of the breast approximately 1080 times. The direction is then reversed and massaged again from inferior to superior direction of the breast 720 times in a circular motion.

The following EXAMPLES are provided.

Example I

An application can include the following three different applications:

Current is applied to mammary glands from 0.8 to 1.8 microseconds. Pulse may be trapezoidal or rectangular in nature with a frequency of about 300 hertz initially. The breast is massaged with 1080 repetitions or from about 15 to about 20 minutes in circular motion both ways for from about 30 to about 90 days or until the desired augmentation is achieved.

Example II

Breast augmentation of the mammary glands is achieved by attaching the cathode to the dorsum and auricular surface of the ear. The anode is attached to the back in the area of the thoracic spine. The frequency is set for 100 to 550 microseconds. Pulse may be rectangular or trapezoidal. The breast is massaged with 1080 repetitions in an upward, circular motion and 720 repetitions or from about 20 to 30 minutes in a downwards, circular motion. The massage motion is reversed each day. The procedure is performed for from about 30 to about 90 days or continued until the desired size and shape is achieved.

Example III

Female subject Carmen, age forty-five (45), height five foot one (5'1"), one hundred seventy pounds (170 lbs.). Subject began with an initial breast volume of two hundred twenty milliliters (220). Breast volume measurements were taken using the water displacement method. Subject began with fifteen (15) minute applications. After one week of herboelectric applications, breast volume was measured at two hundred fifty milliliters (250 ml). After five (5) applications, the subject indicated that both breast were "lifted" and "firm". Subject also indicated that "her bra seemed fuller" but with no discernable change in the color of the breast tissue and not swelling. Subject indicated some soreness of the mammary gland during the first 5 minutes of each application which disappeared.

On the eleventh application of herboelectric stimulation, breast volume was measured at two hundred ninety milliliters (290 ml).

Measurements were again taken about the thirtieth day with a breast volume of three hundred thirty milliliters (330 ml). Subject indicated after 43 applications that her breasts were increasing in size in a manner she experienced during pregnancy.

TABLE I (Subject Carmen)

| Application # | Volume (milliliters) |
|---|---|
| 1 | 220 |
| 5 | 250 |
| 11 | 290 |
| 16 | 310 |
| 21 | 330 |
| 26 | 350 |
| 32 | 375 |

TABLE I-continued (Subject Carmen)

| Application # | Volume (milliliters) |
|---|---|
| 37 | 445 |
| 43 | 500 |
| 44 | 575 |
| 45 | 670 |

TABLE II

System Parameters

| | |
|---|---|
| Intensity: | From about 10 microamperes to about 600 microamperes |
| Frequency: | 300-550 hertz |
| Pulse Rate: | 5-1220 hertz |
| Polarity: | Bi-polar 3 seconds |
| Current Output: | 0-1000 microamperes |
| Output Voltage: | 0-2.5 Volts Peak to Peak 15,000 ohm resistance |
| Voltage: | 8 to 10 Volts |
| Pulse Length: | 0.3-3.6 ms |
| Waveform: | Square or Trapezoidal |
| Current: | 500-800 microamperes |

Other modifications of the present invention may occur to those skilled in the art based upon a review of the present application and these modifications, including equivalents thereof, are intended to be included within the scope of the present invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method for providing non-surgical treatments for breast tissue, comprising the steps of:
    tactile stimulating the breast tissue of a patient by a moving motion to form pressure around the breast; and
    generating electrical current of up to about 1,000 microamperes, and in a frequency range of about 0.5 Hz to about 550 Hz from an electrical generator;
    connecting a first electrode and a second electrode and a third electrode that are connected to the electrical generator;
    clamping a first electrode to clamp to an ear of the patient;
    attaching a second electrode to attach to a hand or finger of the patient; and
    attaching a third electrode to another body area of the patient, wherein the tactile stimulating and electrical generating steps provide breast augmentation to the breast tissue.

2. A method for providing non-surgical treatments for breast tissue, comprising the steps of:
    tactile stimulating the breast tissue of a patient by a moving motion to form pressure;
    generating electrical current of up to about 1,000 microamperes, and in a frequency range of about 0.5 Hz to about 550 Hz from an electrical generator;
    connecting a first electrode and a second electrode and a third electrode that are connected to the electrical generator;
    clamping a first electrode to clamp to an ear of the patient;
    attaching a second electrode to attach to a hand or finger of the patient; and
    attaching a third electrode to another body area of the patient, wherein the tactile stimulating and electrical generating steps provide anti-carcinogenic treatment to the breast tissue.

3. The methods of claims 1 or 2, wherein the stimulating step includes:
    massaging the breast tissue.

4. The methods of claim 1 or 2, wherein the stimulating step further includes:
    rubbing a natural based solution into the breast tissue.

5. The methods of claim 1 or 2, wherein the generating of the electrical current includes the step of:
    generating the electrical current having a frequency between about 300 Hz to about 550 Hz.

6. The method of claim 4, wherein the natural based solution includes pomegranate.

7. The methods of claim 1 or 2, wherein the clamping step includes the steps of:
    providing a first clamp member and a second clamp member; and
    compressing a portion of the ear between the first and second clamp members.

* * * * *